(12) United States Patent
Shanks et al.

(10) Patent No.: US 8,083,785 B2
(45) Date of Patent: *Dec. 27, 2011

(54) MULTI-PROBE LASER DEVICE

(75) Inventors: Steven C. Shanks, Mesa, AZ (US);
Kevin B. Tucek, Gilbert, AZ (US)

(73) Assignee: Erchonia Corporation, McKinney, TX (US)

( * ) Notice: Subject to any disclaimer, the term of this patent is extended or adjusted under 35 U.S.C. 154(b) by 1399 days.

This patent is subject to a terminal disclaimer.

(21) Appl. No.: 10/612,504

(22) Filed: Jul. 1, 2003

(65) Prior Publication Data

US 2004/0006378 A1 Jan. 8, 2004

(51) Int. Cl.
*A61N 5/067* (2006.01)
(52) U.S. Cl. .............................. 607/89; 606/9
(58) Field of Classification Search .............. 607/88–94; 606/9

See application file for complete search history.

(56) References Cited

U.S. PATENT DOCUMENTS

| | | | |
|---|---|---|---|
| 4,784,135 A | 11/1988 | Blum et al. | |
| 4,905,690 A | 3/1990 | Ohshiro et al. | |
| 4,930,504 A * | 6/1990 | Diamantopoulos et al. | 607/88 |
| 5,150,704 A * | 9/1992 | Tatebayashi et al. | 607/89 |
| 5,474,528 A | 12/1995 | Meserol | |
| 5,653,706 A * | 8/1997 | Zavislan et al. | 606/9 |
| 5,755,752 A | 5/1998 | Segal | |
| 6,063,108 A * | 5/2000 | Salansky et al. | 607/89 |
| 6,074,411 A * | 6/2000 | Lai et al. | 607/89 |
| 6,110,195 A * | 8/2000 | Xie et al. | 607/89 |
| 6,267,779 B1 * | 7/2001 | Gerdes | 607/89 |
| 6,273,885 B1 * | 8/2001 | Koop et al. | 606/9 |
| 6,413,267 B1 * | 7/2002 | Dumoulin-White et al. | 607/89 |
| 2002/0002391 A1 | 1/2002 | Gerdes | |
| 2002/0071287 A1 | 6/2002 | Haase | |
| 2005/0203592 A1 * | 9/2005 | Teichert | 607/88 |

* cited by examiner

*Primary Examiner* — Henry M Johnson, III
(74) *Attorney, Agent, or Firm* — Etherton Law Group, LLC; Sandra L. Etherton; Benjamin D. Tietgen

(57) ABSTRACT

A hand-held laser device that can simultaneously provide multiple types of low level laser therapy treatments to multiple areas of a patient's body simultaneously. The device enables laser light of different pulse repetition rate, different beam shapes and spot sizes to be applied to a patient's body. The device includes multiple laser sources. In the preferred embodiment, two semiconductor diode laser sources simultaneously provide two separate laser beams from separate probes, one laser beam producing laser light at a first pulse repetition rate and the other producing laser light at a second pulse repetition rate.

3 Claims, 6 Drawing Sheets

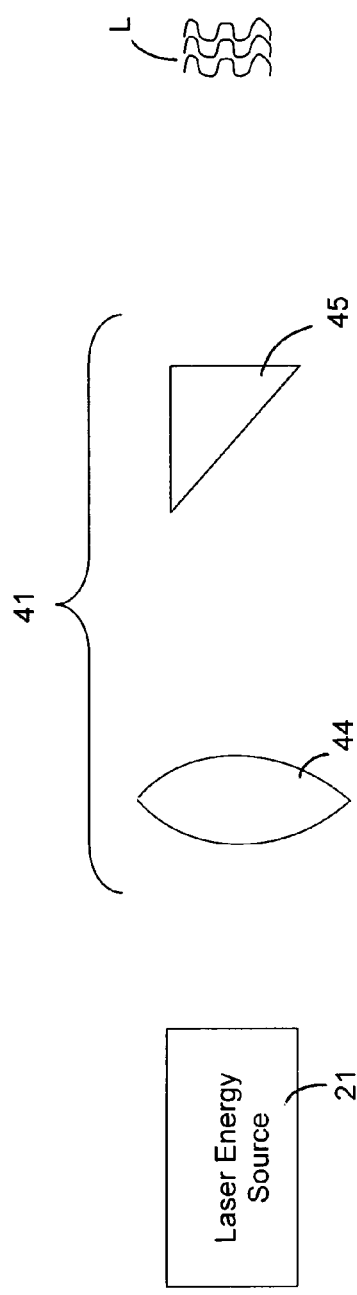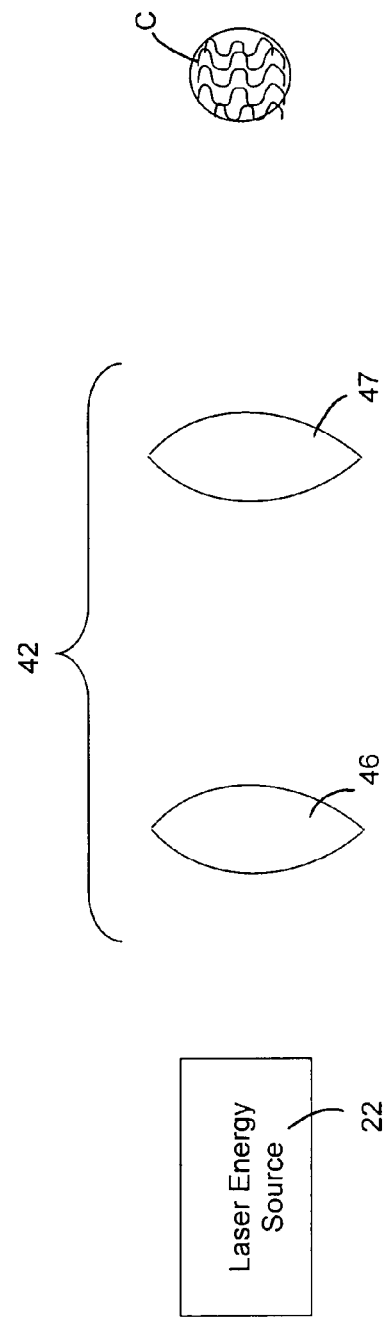

MULTI-PROBE LASER DEVICE

CROSS-REFERENCE TO RELATED APPLICATIONS

This application claims the benefit of U.S. patent application Ser. No. 09/932,907 filed Aug. 20, 2001, now U.S. Pat. No. 6,746,473 which claims the benefit of U.S. Provisional Application No. 60/273,282 filed Mar. 2, 2001.

FIELD OF INVENTION

This invention relates generally to medical devices that employ lasers. More particularly, this invention relates to a laser light generator device that has multiple probes, enabling multiple different treatments to be made simultaneously.

BACKGROUND

Low energy laser therapy (LLLT) is used in the treatment of a broad range of conditions. LLLT improves wound healing, reduces edema, and relieves pain of various etiologies, including successful application post-operatively to liposuction to reduce inflammation and pain. LLLT is also used during liposuction procedures to facilitate removal of fat by causing intracellular fat to be released into the interstice. It is also used in the treatment and repair of injured muscles and tendons.

LLLT utilizes low level laser energy, that is, the treatment has a dose rate that causes no immediate detectable temperature rise of the treated tissue and no macroscopically visible changes in tissue structure. Consequently, the treated and surrounding tissue is not heated and is not damaged. There are a number of variables in laser therapy including the wavelength of the laser beam, the area impinged by the laser beam, laser energy, pulse repetition rate, treatment duration and tissue characteristics. The success of each therapy depends on the relationship and combination of these variables. For example, liposuction may be facilitated with one regimen utilizing a given wavelength and treatment duration, whereas pain may be treated with a regimen utilizing a different wavelength and treatment duration, and inflammation a third regimen. Specific devices are known in the art for each type of therapy.

Often it is desirable to treat a patient for multiple types of problems during a single treatment. Because specific therapies require different regimen, treating multiple problems currently requires multiple separate laser devices. It is desirable to provide a device that enables multiple types of treatments with a single device. It is also desirable to be able to provide multiple treatments simultaneously with a single device, in different areas of a patient's body.

Therefore, an object of this invention is to provide a laser therapy device that enables multiple types of treatments. It is another object to provide a single device that provides these treatments simultaneously. It is another object of this invention to provide an apparatus that can simultaneously emit multiple beams of laser light that can be applied to multiple areas of a patient's body. It is another object of this invention to provide an apparatus that can simultaneously emit laser light in multiple different pulse repetition rates. It is a further object of this invention to provide an apparatus that can simultaneously emit laser light in multiple beam shapes and spot sizes. It is a particular object of this invention to provide a hand-held therapeutic laser device to provide low level laser therapy which can be used to simultaneously facilitate liposuction, treat post-operative inflammation and pain, and treat and repair injured muscles and tendons.

SUMMARY OF THE INVENTION

This invention is an improved hand-held laser device that can simultaneously provide multiple types of low level laser therapy treatments to multiple areas of a patient's body simultaneously. The device enables laser light of different pulse repetition rates, different beam shapes and spot sizes to be applied to a patients body. The device includes multiple laser sources. In the preferred embodiment, two semiconductor diode laser sources simultaneously provide two separate laser beams from separate probes, one laser beam producing laser light at a first pulse repetition rate and the other producing laser light at a second pulse repetition rate.

BRIEF DESCRIPTION OF THE DRAWINGS

FIG. 2 is a schematic view of the optical arrangement producing a line spot shape of the preferred embodiment.

FIG. 3 is a schematic view of the optical arrangement producing a circular spot shape of the preferred embodiment.

DETAILED DESCRIPTION OF THE INVENTION

Figure 1:
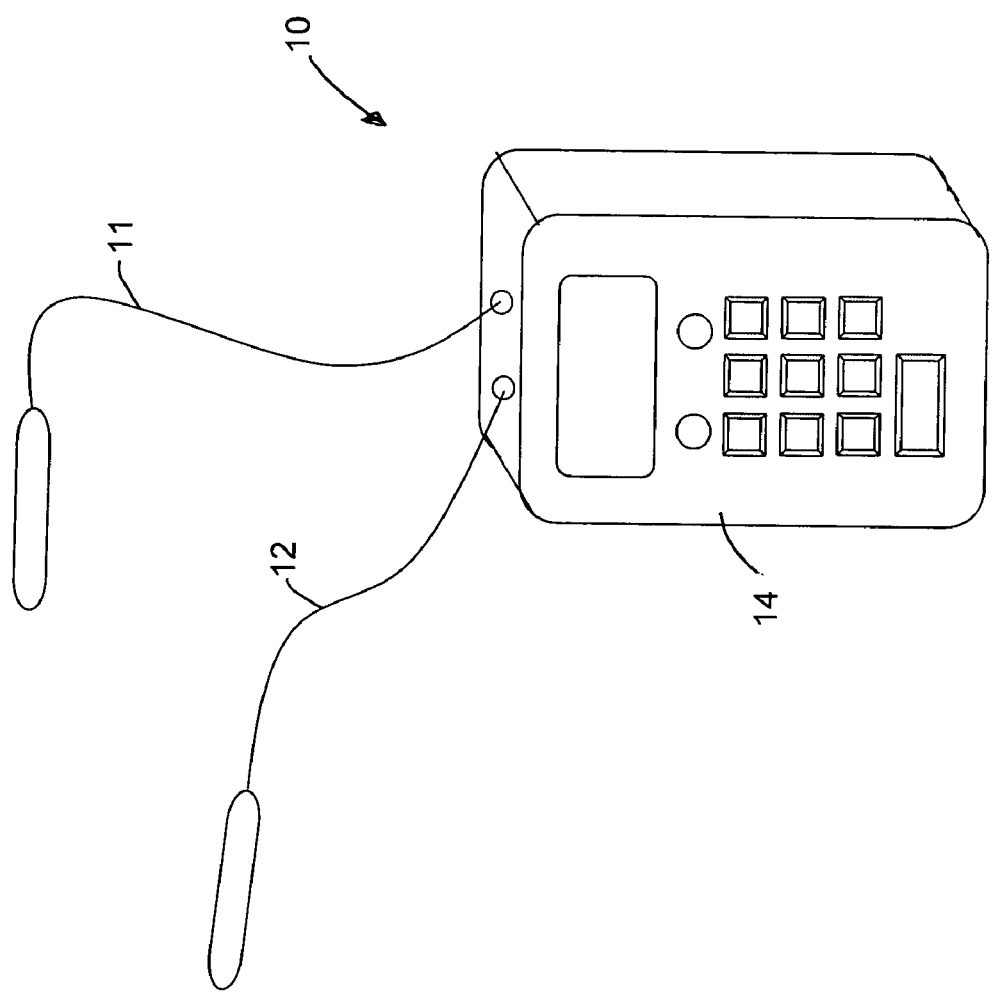
FIG. 1 is a schematic illustration of a preferred embodiment of the present invention.

Referring to the drawings, there is illustrated a hand-held laser device designated generally as 10. The device includes one or more laser energy sources, a power source, at least two optical arrangements, one or more control circuits, and at least two hand-held aiming devices, referred to herein as probes. FIG. 1 shows the preferred embodiment in which a first probe 11 and a second probe 12 are connected to a base 14, which includes a power source 15 (not shown). The base 14 is typically a hand-held unit, but it may also be a stationary unit that typically sits on a table or the ground, functioning as a central base from which many probes may be employed.

The preferred embodiment comprises a first laser energy source 21 for emitting light from the first probe 11 and a second laser energy source 22 for emitting light from the second probe 12. The laser energy sources 21 and 22 are connected to the power source 15. The power source preferably provides direct current, such as that provided by a battery, but may instead provide alternating current such as that provided by conventional building current which is then converted to direct current. These laser energy sources can be energized independently or simultaneously, which throughout this specification refers to acts occurring at generally at the same time.

The first laser energy source 21 and second laser energy source 22 each produce a laser beam which exits the laser and is shone through optical arrangements 41 and 42, respectively, that produce beam spots. The beam spot is the crosssectional shape and size of the emitted beam as it exits the optical arrangement. For example, a laser beam of circular cross-section creates a circular beam spot as the laser light impinges the patient's skin. If the laser light emitted is in the visible range, a circular spot can be seen on the patient's skin of substantially the same diameter as the laser beam emitted from the optics arrangement. Various beam spot shapes can be created, including a line, a circle, an ellipse, a plus-sign, or combination of any of them. The probes may product different spot shapes, or have the same spot shapes.

In the preferred embodiment, the first laser beam is passed through a first optical arrangement that generates a beam of substantially linear cross-section, resulting in a line of laser light seen on the patient's skin. The second laser passes through a second optical arrangement that generates a beam of circular cross-section, resulting in a circular spot shape as seen on the patient's skin. FIG. 2 illustrates the first optical arrangement 41 of the preferred device, which includes a collimating lens 44 and a line generating prism 45. The collimating lens 44 and the line generating prism 45 are disposed in serial relation to the laser energy source 21. The collimating lens 44 and the line generating prism 45 receive and transform the generated beam of laser light into the line of laser light L. As an alternative, a suitable electrical or mechanical arrangement could be substituted for the optical arrangement 41.

As shown in FIG. 3 the second optical arrangement 42 of the preferred device includes a collimating lens 46 and a beam spot shaping lens 47. As with the first optical arrangement, the collimating lens 46 and beam spot shaping lens 47 are disposed in serial relation to the second laser energy source 22. The collimating lens 46 and beam spot shaping lens 47 receive and transform the generated beam of laser light into a circular beam spot of laser light C. As an alternative, a suitable electrical or mechanical arrangement could be substituted for the optical arrangement 42 to achieve a desired spot shape.

Control circuitry is connected to the laser energy sources to control whether the lasers are on or off, how long the lasers are powered on, the duration of each pulse of laser light emitted, and the period of time between one pulse starting and the next pulse starting, which, in combination with the duration of each pulse is referred to herein as the pulse repetition rate. Typically the control circuitry is digital, in discrete or integrated circuits, as is known in the art, but analog circuits can also be employed. In the preferred embodiment there are separate control circuits for each probe. Control circuits 31 and 32 are connected to the laser energy sources 21 and 22, respectively, to control the various parameters of the emissions. For ease of reference, pulse repetition rates can be referred to in shorthand notation in pulses/second, or Hz. Pulse repetition rates from 0 to 100,000 Hz may be employed to achieve the desired effect on the patient's tissue. At 100,000 Hz, the pulse repetition, rate is 0.00001 second. At 0 Hz, a continuous beam of laser light is generated. The goal for LLLT regimen is to deliver laser energy to the target tissue utilizing a pulse repetition, rate short enough to sufficiently energize the targeted tissue and avoid thermal damage to adjacent tissue.

Figure 4:
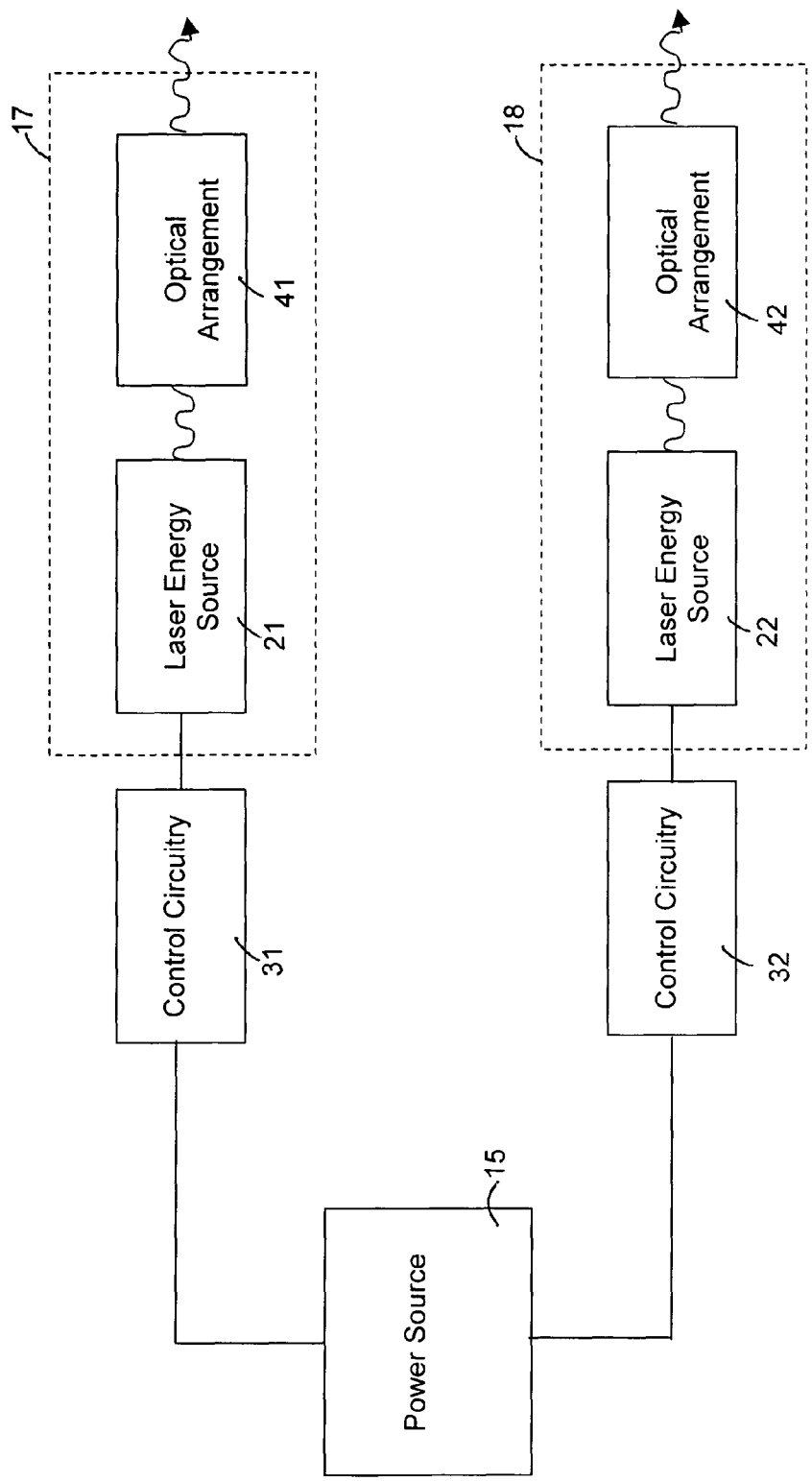
FIG. 4 is a schematic illustration of a preferred embodiment of the present invention, where the dotted line defines the components disposed in each probe.
Figure 5:
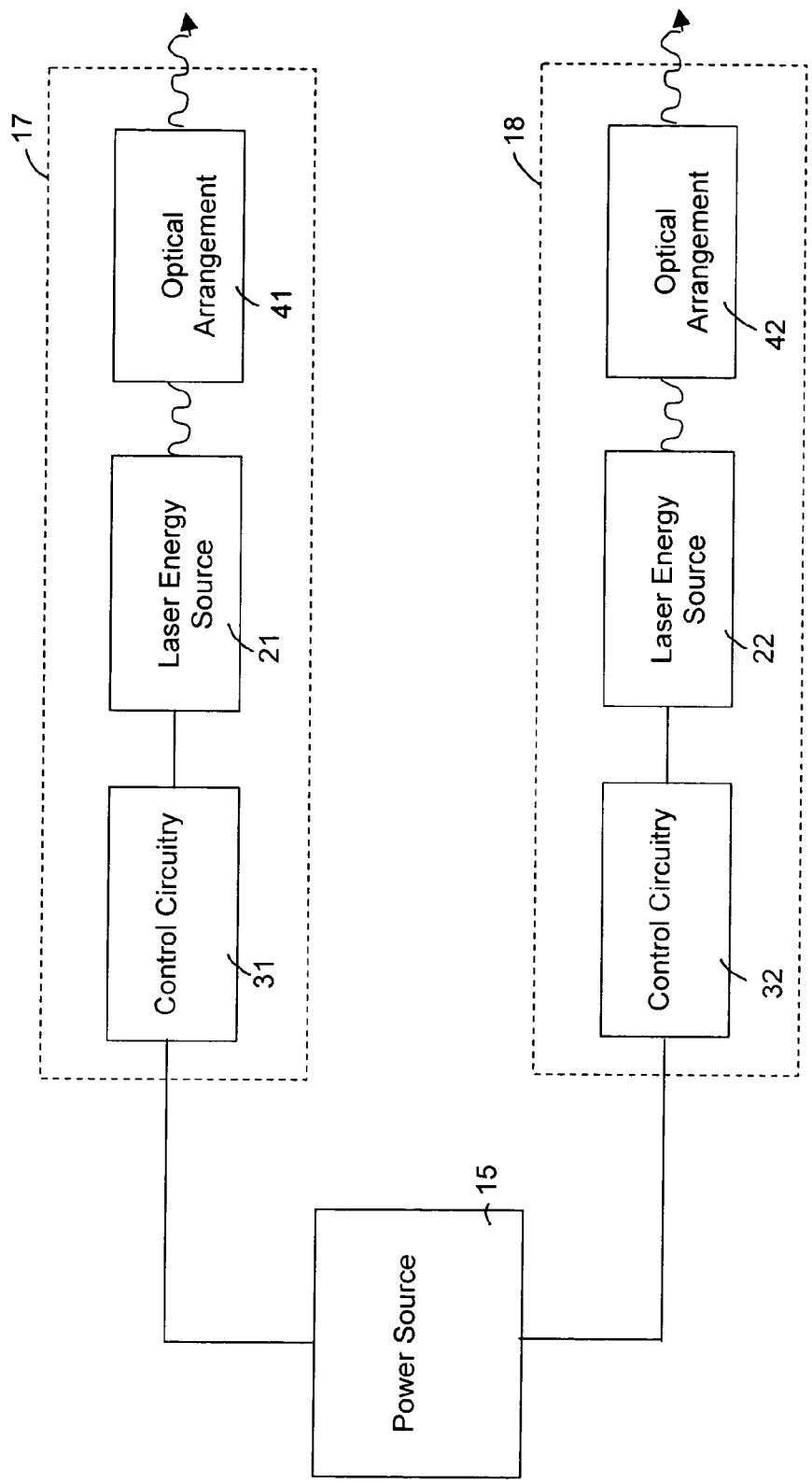
FIG. 5 is a schematic illustration of an alternate embodiment of the present invention, where the dotted line defines the components disposed in each probe.
Figure 6:
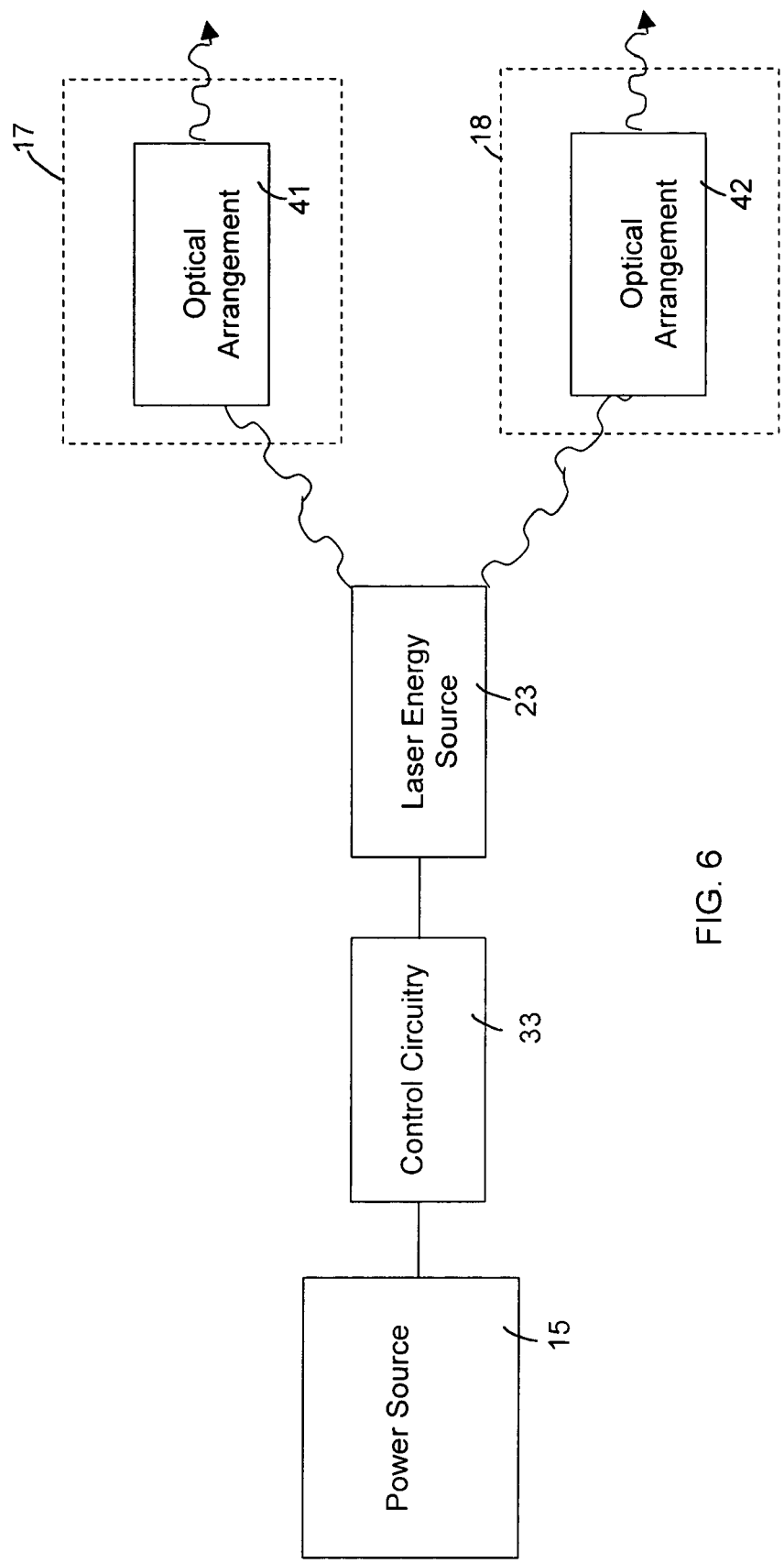
FIG. 6 is a schematic illustration of an alternate embodiment of the present invention, where the dotted line defines the components disposed in each probe.

The probes have an interior cavity. In the preferred embodiment, the first laser energy source 21 and first optical arrangement 41 are contained in the first probe 11 and the second laser energy source 22 and second optical arrangement 42 are contained in the second probe 12, while the power source 15 and control circuitry 31 and 32 are contained within the base 14. See FIG. 4, which illustrates the configuration of the components of the invention as they relate to each probe, and where the dotted line 17 indicates the components disposed in the first probe and dotted line 18 indicates the components disposed in the second probe. Alternatively, the laser energy source, optical arrangement, and control circuitry can be housed in the probe. That is, the first laser energy source 21, the first optical arrangement 41, and the control circuitry for the first probe 31 are contained in the first probe 11, and the second laser energy source 22, the second optical arrangement 42, and the control circuitry for the second probe 32 are contained in the second probe 12, as the power source 15 remains within the base 14. See FIG. 5 in which dotted lines 17 and 18 again indicate the components that are in the probes. FIG. 6 shows another alternate configuration, in which a single laser energy source 23, a single control circuitry 33 for the first probe and the second probe, and the power source 15 are contained in the base 14, and the probes contain only the optical arrangement for the first probe 41 and the optical arrangement for the second probe 42, respectively. Again, the dotted lines 17 and 18 indicate which components are in the probes.

Laser energy sources are known in the art for use in low-level laser therapy. Visible light in about the 400-700 nm range is preferred, and the frequency is determined by the particular therapy given to the patient. The laser energy sources include Helium-Neon lasers having a 632 nm wavelength and semiconductor diode lasers with a broad range of wavelengths between about 600-800 nm. The laser energy sources in the preferred embodiment are two semiconductor laser diodes that produce light in the red range of the visible spectrum, having a wavelength of about 635 nm. Other suitable wavelengths are used for other particular applications. While many LLLT regimen include visible laser light, it may be advantageous to utilize ultraviolet (approx. 1-400 nm) or infrared (approx 700-$10^5$ nm) laser energy, again depending on the type of treatment desired. Solid state and tunable semiconductor laser diodes may also be employed to achieve the desired wavelength.

Different therapy regimens require diodes of different wattages. The preferred laser diodes use less than one watt of power each to simultaneously facilitate liposuction, treat post-operative inflammation, and post-operative pain. Diodes of various other wattages may also be employed to achieve the desired laser energy for the given regimen.

Figure 7:
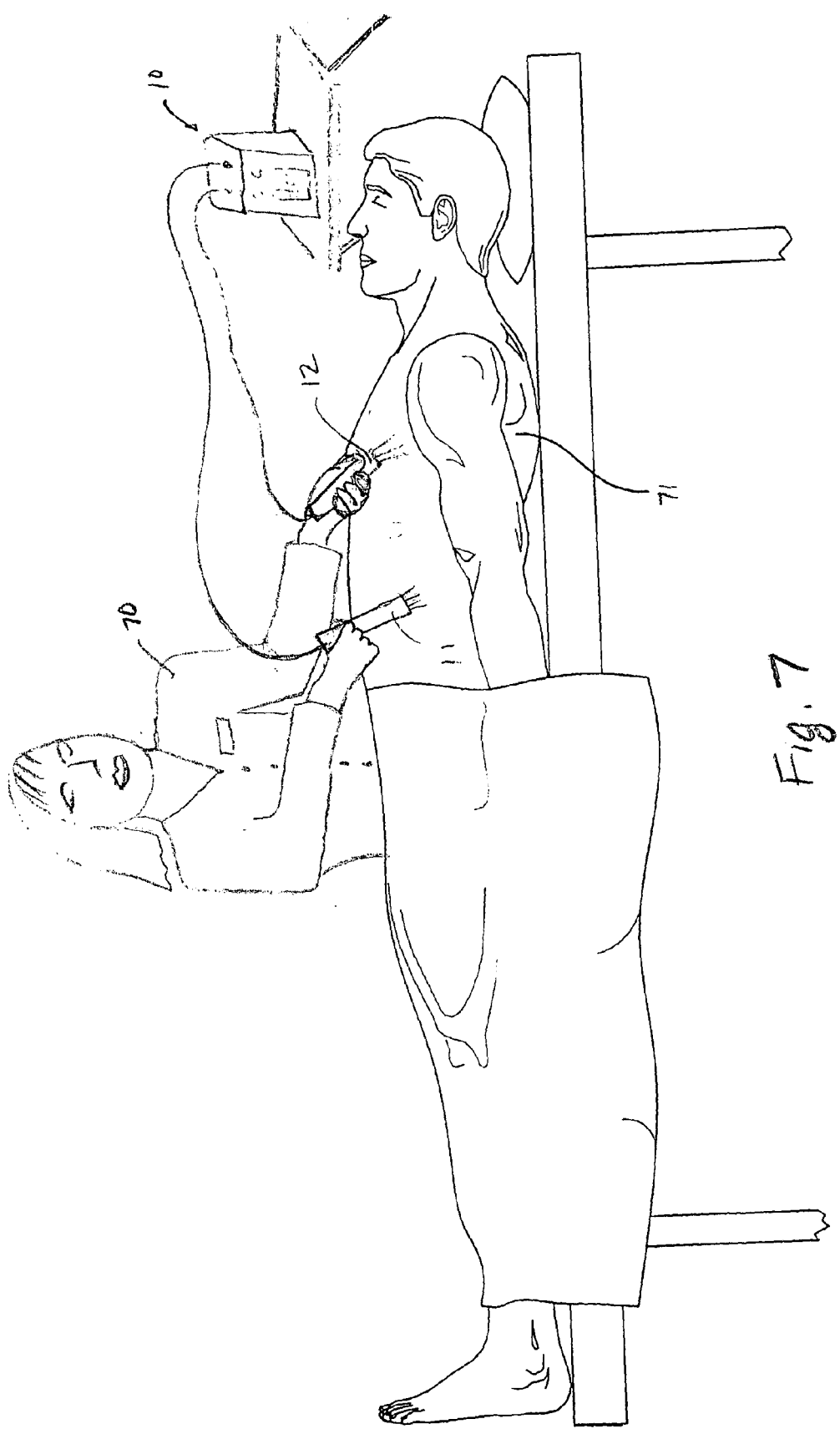
FIG. 7 is a schematic illustration of application of low-level laser radiation using the preferred embodiment of the present invention.

FIG. 7 illustrates the device in use. A practitioner 70 treats one area of the patient 71 with the first probe 11 and treats a different area of the patient 71 with the second probe 12.

While there has been illustrated and described what is at present considered to be a preferred embodiment of the present invention, it will be understood by those skilled in the art that various changes and modifications may be made, and equivalents may be substituted for elements thereof without departing from the true scope of the invention. Therefore, it is intended that this invention not be limited to the particular embodiment disclosed as the best mode contemplated for carrying out the invention, but that the invention will include all embodiments falling within the scope of the appended claims.

We claim:

1. A multi-probe device comprising:
   a) two or more laser energy sources, each generating one or more laser beams:
   b) two or more handheld probes from which the laser beams emit, wherein:
      i. each of the handheld probes houses one or more laser energy sources therewithin and at least one laser energy source generates a laser beam having a wavelength in the ultraviolet range; and ii. each of the handheld probes emits one or more laser beams, and each of the handheld probes is not connected to a support structure while being freely moved by a user's hand relative to the surface of the skin of a patient; and c) an optical arrangement attached to each handheld probe for receiving one or more laser beams and for transforming each of the laser beams into a desired spot shape.

2. A multi-probe device comprising:

d) two or more laser energy sources, each generating one or more laser beams;

e) two or more handheld probes from which the laser beams emit, wherein:

i. each of the handheld probes houses one or more laser energy sources therewithin; and ii. each of the handheld probes emits one or more laser beams, and each of the handheld probes is not connected to a support structure while being freely moved by a user's hand relative to the surface of the skin of a patient; and f) an optical arrangement attached to each handheld probe for receiving one or more laser beams and for transforming each of the laser beams into a desired spot shape, wherein a first laser beam has a first spot shape and a second laser beam has a second spot shape wherein the first spot shape is different from the second spot shape.

3. A therapeutic laser device comprising:

a) a first semiconductor diode laser energy source generating a first laser beam and a second semiconductor diode laser energy source generating a second laser beam;

b) a first handheld probe from which the first laser beam emits, the first handheld probe having an interior cavity that houses the first semiconductor laser energy source therewithin and that is freely moved by the user's hand relative to the surface of the skin of a patient while emitting the first laser beam;

c) an optical arrangement mounted in the interior cavity of the first handheld probe for receiving the first laser beam and for transforming the first laser beam into a desired spot shape;

d) a second handheld probe from which the second laser beam emits, the second handheld probe having an interior cavity that houses the second semiconductor laser energy source therewithin and that is freely moved by the user's hand relative to the surface of the skin of a patient and relative to the first handheld probe while emitting a laser beam;

e) an optical arrangement mounted in the interior cavity of the second handheld probe for receiving the second laser beam and for transforming the second laser beam into a desired spot shape; and f) a control circuit for independently controlling each of the generated laser beams; and g) wherein the first and second handheld probes are not connected to a support structure while being freely moved relative to the surface of the skin of a patient and wherein at least one laser energy source generates a laser beam having a wavelength in the ultraviolet range.

\* \* \* \* \*